(12) United States Patent
Bencsits

(10) Patent No.: US 7,144,591 B2
(45) Date of Patent: Dec. 5, 2006

(54) COMPOSITION CONTAINING CITRONELLA JAVA OIL AND USE THEREOF FOR REPELLING INSECTS

(75) Inventor: Franz Bencsits, Klosterneuburg (AT)

(73) Assignee: Fulltec AG, Zug (CH)

( * ) Notice: Subject to any disclaimer, the term of this patent is extended or adjusted under 35 U.S.C. 154(b) by 0 days.

(21) Appl. No.: 10/512,610

(22) PCT Filed: Apr. 15, 2003

(86) PCT No.: PCT/EP03/03944

§ 371 (c)(1),
(2), (4) Date: May 27, 2005

(87) PCT Pub. No.: WO03/092383

PCT Pub. Date: Nov. 13, 2003

(65) Prior Publication Data

US 2005/0260239 A1    Nov. 24, 2005

(30) Foreign Application Priority Data

Apr. 29, 2002 (DE) .................... 102 19 109

(51) Int. Cl.
*A01N 65/00* (2006.01)
*A01N 25/34* (2006.01)

(52) U.S. Cl. .................... 424/725; 424/403

(58) Field of Classification Search ........... 424/725, 424/403
See application file for complete search history.

(56) References Cited

U.S. PATENT DOCUMENTS

| 5,106,622 | A |   | 4/1992 | Sherwood et al. |
| 5,614,484 | A |   | 3/1997 | Panandiker |
| 5,753,264 | A | * | 5/1998 | Magdassi et al. |

FOREIGN PATENT DOCUMENTS

| EP | 0630571 | 12/1994 |
| SE | 9800767 | 9/1999 |
| WO | WO 93/04158 | 3/1993 |

OTHER PUBLICATIONS

Labinas, A. M. et al. Acta Scientiarum 24(5): 1401-1405. Effect of Java grass (Cymbopogon winterianus Jowitt essential oil on fall armyworm Spodoptera frugiperda (J. E. Smith, 1797) (Lepidoptera, Noctuidae.*
http://www.annals.org/cgi/content/full128/11/931, downloaded Apr. 17, 2006. Fradin, M. S. Annals of Internal Medicine (1998), 128(11): 931-940. Mosquitoes and mosquito repellants.*
International Search Report for PCT/EP03/03944 dated Aug. 6, 2003.

* cited by examiner

*Primary Examiner*—Michele Flood
(74) *Attorney, Agent, or Firm*—Kilyk & Bowersox, P.L.L.C.

(57) ABSTRACT

The present invention concerns a composition comprising a specific ethereal oil, which may be used as insect repellent.

21 Claims, 8 Drawing Sheets

Results of the activity of the single substances and the mixtures not within the compositions in accordance with the present invention and the reference product ANTI BRUMM, comprising as active component 30% N,N-diethyl-m-toluamide against *Aedes aegypti*:

| 1 | 2 | | | | | | | | | | | | | | | | | | | |
|---|---|---|---|---|---|---|---|---|---|---|---|---|---|---|---|---|---|---|---|---|
| Product | a | b | c | d | a | B | c | d | a | b | c | d | a | b | c | d | a | b | c | d |
| | PC1 | | | | PC2 | | | | PC3 | | | | PC4 | | | | PC5 | | | |
| 1 | # | 5 | 3* | | # | 3 | 2* | | # | 11 | 4* | | # | 16 | 9* | | # | 5 | 2* | |

| | | | | | | | | | | | | | | | | |
|---|---|---|---|---|---|---|---|---|---|---|---|---|---|---|---|---|
| a | b | c | d | a | b | c | d | a | b | c | d |
| PC6 | | | | PC7 | | | | PC8 | | | |
| # | 6 | 3* | | # | 7 | 3* | | # | 5 | 2* | |

| 1 | 2 | | | | | | | | | | | | | | | | | | | |
|---|---|---|---|---|---|---|---|---|---|---|---|---|---|---|---|---|---|---|---|---|
| Product | a | b | c | d | a | b | c | d | a | b | c | d | a | b | c | d | a | b | c | d |
| | PC9 | | | | PC10 | | | | PC11 | | | | PC12 | | | | PC13 | | | |
| 1 | # | 12 | 4* | | # | 10 | 4* | | # | 6 | 2* | | # | 7 | 3* | | # | 4 | 1* | |

| | | | | | | | | | | | | | | | | |
|---|---|---|---|---|---|---|---|---|---|---|---|---|---|---|---|---|
| a | b | c | d | a | b | c | d | a | b | c | d |
| PC14 | | | | PC15 | | | | PC16 | | | |
| # | 8 | 3* | | # | 5 | 2* | | # | 12 | 4* | |

Figure 1

Confirmatory tests using PC1, 2, 3, 4 and employing diferent test persons at a different time and with diferent specimen of A. aegypti:

| | | PC1 | | | PC2 | | | | PC3 | | | | PC4 | | | |
|---|---|---|---|---|---|---|---|---|---|---|---|---|---|---|---|---|
| | a | b | c | d | a | b | c | d | a | b | c | d | a | b | c | d |
| Product | | | | | | | | | | | | | | | | |
| 1 | # | # | 8 | 4* | # | # | 5 | 2* | # | # | 6 | 2* | # | # | 13 | 7* |

Figure 2a

Reference product:

| | a | b | c | d |
|---|---|---|---|---|
| 1 | 130 | 4 | 0 | 0 |
| 2 | 150 | 32 | 2 | 0 |
| 3 | 150 | 45 | 9 | 0 |
| 4 | 180 | 30 | 8 | 2* |

Figure 2b

Results regarding the activity of compositions according to the present invention concerning the repellence against A. aegypti:

Remarks: (x) at parameter d = minute of the first bite during the 10 minute test period

| 1 | 2 | A | b | c | d | a | b | c | d | A | b | c | d | a | b | c | d |
|---|---|---|---|---|---|---|---|---|---|---|---|---|---|---|---|---|---|
|   | Product | | WS1 | | | | WS2 | | | | WS3 | | | | WS4 | | |
| 1 | 10 | 120 | 5 | 1 | 0 | 130 | 8 | 2 | 0 | 130 | 0 | 0 | 0 | 120 | 3 | 0 | 0 |
| 2 | 10 | 130 | 14 | 4 | 1 (8)* | 130 | 16 | 6 | 2 (5)* | 130 | 8 | 2 | 0 | 120 | 11 | 4 | 0 |
| 3 | 10 | | | | | | | | | 100 | 21 | 6 | 2 (6)* | 110 | 23 | 7 | 3 (4)* |

| Product | A | WS9 b | c | d | a | WS10 b | c | d | A | WS13 b | c | d | a | WS14 b | c | d |
|---|---|---|---|---|---|---|---|---|---|---|---|---|---|---|---|---|
| 1 | 150 | 0 | 0 | 0 | 120 | 0 | 0 | 0 | 130 | 0 | 0 | 0 | 140 | 0 | 0 | 0 |
| 2 | 120 | 3 | 0 | 0 | 110 | 0 | 0 | 0 | 140 | 2 | 0 | 0 | 130 | 0 | 0 | 0 |
| 3 | 100 | 12 | 3 | 0 | 120 | 6 | 0 | 0 | 100 | 4 | 0 | 0 | 120 | 4 | 0 | 0 |
| 4 | 90 | 23 | 7 | 3 (3)* | 110 | 12 | 3 | 1 (5)* | 130 | 10 | 1 | 0 | 140 | 7 | 0 | 0 |
| 5 |  |  |  |  |  |  |  |  | 80 | 18 | 5 | 3 (4)* | 100 | 8 | 3 | 1 (9)* |

Figure 3c

| Product | A | WS17 b | c | d | a | WS18 b | c | d | A | WS19 b | c | d | a | WS20 b | c | d |
|---|---|---|---|---|---|---|---|---|---|---|---|---|---|---|---|---|
| 1 | 110 | 0 | 0 | 0 | 120 | 0 | 0 | 0 | 150 | 0 | 0 | 0 | 120 | 0 | 0 | 0 |
| 2 | 110 | 0 | 0 | 0 | 130 | 0 | 0 | 0 | 120 | 0 | 0 | 0 | 130 | 0 | 0 | 0 |
| 3 | 120 | 0 | 0 | 0 | 130 | 0 | 1 | 0 | 130 | 0 | 1 | 0 | 120 | 0 | 0 | 0 |
| 4 | 120 | 3 | 5 | 0 | 120 | 5 | 4 | 0 | 110 | 4 | 5 | 0 | 110 | 0 | 0 | 0 |
| 5 | 110 | 11 | 8 | 0 | 100 | 12 | 6 | 0 | 100 | 21 | 7 | 0 | 100 | 16 | 2 | 0 |
| 6 | 70 | 14 | 3 | 0 | 100 | 23 | 3 | 0 | 100 | 23 | 4 | 0 | 80 | 14 | 2 | 0 |
| 7 | 70 | 3 | 0 | 3 (2)* | 90 | 3 | 3 | 3 (3)* | 100 | 10 | 2 | 2 (2)* | 80 | 35 | 15 | 3 (8)* |
| 8 |  |  |  |  |  |  |  |  | 50 | 10 | | | | | | |

Confirmatory tests using WS17, WS18, WS19, WS20 employing different test persons at different times and different specimen of A. aegypti:

| 1 | 2 | A | b | c | d | a | b | c | d | a | b | c | d | a | b | c | d |
|---|---|---|---|---|---|---|---|---|---|---|---|---|---|---|---|---|---|
| Product | | | WS17 | | | | WS18 | | | | WS19 | | | | WS20 | | |
| 1 | 10 | 130 | 0 | 0 | 0 | 110 | 0 | 0 | 0 | 90 | 0 | 0 | 0 | 90 | 0 | 0 | 0 |
| 2 | 10 | 130 | 0 | 0 | 0 | 110 | 0 | 0 | 0 | 110 | 0 | 0 | 0 | 120 | 0 | 0 | 0 |
| 3 | 10 | 130 | 0 | 0 | 0 | 110 | 0 | 0 | 0 | 100 | 0 | 0 | 0 | 110 | 0 | 0 | 0 |
| 4 | 10 | 100 | 5 | 1 | 0 | 110 | 8 | 2 | 0 | 120 | 0 | 3 | 0 | 120 | 0 | 0 | 0 |
| 5 | 10 | 100 | 9 | 3 | 0 | 110 | 15 | 6 | 0 | 120 | 17 | 10 | 0 | 120 | 11 | 0 | 0 |
| 6 | 10 | 80 | 17 | 7 | 0 | 80 | 28 | 12 | 2 (10)* | 80 | 25 | 15 | 0 | 100 | | | |
| 7 | 10 | 60 | 4 | 4 | 1 (1)* | | | | | 70 | 25 | 15 | 3 (9)* | 90 | 18 | 4 | 0 |
| 8 | 10 | | | | | | | | | | | | | 30 | 15 | 8 | 2 (4)* |

Figure 4

| 1 | 2 | A | b | c | d | a | b | c | d | a | b | c | d | a | b | c | d |
|---|---|---|---|---|---|---|---|---|---|---|---|---|---|---|---|---|---|
| Product | | | WS11 | | | WS12 | | | | WS15 | | | | WS16 | | | |
| 1 | 10 | 70 | 0 | 0 | 0 | 100 | 0 | 0 | 0 | 120 | 0 | 0 | 0 | 140 | 0 | 0 | 0 |
| 2 | 10 | 100 | 0 | 0 | 0 | 130 | 0 | 0 | 0 | 120 | 0 | 0 | 0 | 130 | 0 | 0 | 0 |
| 3 | 10 | 110 | 0 | 0 | 0 | 120 | 0 | 0 | 0 | 120 | 0 | 0 | 0 | 130 | 0 | 0 | 0 |
| 4 | 10 | 120 | 2 | 0 | 0 | 120 | 3 | 2 | 0 | 100 | 0 | 0 | 0 | 100 | 0 | 0 | 0 |
| 5 | 10 | 80 | 10 | 2 | 0 | 120 | 8 | 3 | 0 | 100 | 11 | 8 | 0 | 90 | 3 | 0 | 0 |
| 6 | 10 | 80 | 13 | 4 | 0 | 100 | 12 | 6 | 0 | 100 | 28 | 17 | 3 (3)* | 90 | 10 | 3 | 0 |
| 7 | 10 | 60 | 2 | 2 | 2 (2)* | 40 | 2 | 2 | 2 (1)* | | | | | 70 | 14 | 7 | 2 (6)* |

Figure 5

| Product | A | WS5 | | | WS6 | | | | WS7 | | | | WS8 | | | |
|---|---|---|---|---|---|---|---|---|---|---|---|---|---|---|---|---|
| | | b | c | d | a | b | c | d | a | b | c | d | a | b | c | d |
| 1 | 120 | 0 | 0 | 0 | 110 | 0 | 0 | 0 | 100 | 0 | 0 | 0 | 110 | 0 | 0 | 0 |
| 2 | 130 | 0 | 0 | 0 | 120 | 0 | 0 | 0 | 110 | 0 | 0 | 0 | 110 | 0 | 0 | 0 |
| 3 | 130 | 0 | 0 | 0 | 110 | 0 | 0 | 0 | 100 | 0 | 0 | 0 | 120 | 0 | 0 | 0 |
| 4 | 120 | 0 | 0 | 0 | 130 | 0 | 0 | 0 | 110 | 0 | 0 | 0 | 120 | 0 | 0 | 0 |
| 5 | 120 | 0 | 0 | 0 | 130 | 0 | 0 | 0 | 110 | 0 | 0 | 0 | 120 | 0 | 0 | 0 |
| 6 | 120 | 0 | 0 | 0 | 130 | 2 | 2 | 0 | 110 | 0 | 0 | 0 | 120 | 2 | 0 | 0 |
| 7 | 120 | 2 | 0 | 0 | 120 | 8 | 0 | 0 | 110 | 10 | 0 | 0 | 120 | 4 | 0 | 0 |
| 8 | 120 | 2 | 0 | 0 | 130 | 25 | 3 | 0 | 100 | 10 | 0 | 0 | 110 | 22 | 1 | 0 |
| 9 | 120 | 8 | 4 | 0 | 140 | 35 | 16 | 0 | 100 | 5 | 1 | 0 | 110 | 35 | 3 | 0 |
| 10 | 120 | 26 | 12 | 0 | 100 | 30 | 2 | 0 | 80 | 7 | 4 | 0 | 110 | 38 | 14 | 0 |
| 11 | 90 | 3 | 3 | 3 (1)* | 30 | 5 | | 2 (2)* | 80 | 7 | | 2 (4)* | 20 | 12 | 8 | 3 (2)* |
| 12 | 10 | | | | | | | | 40 | | | | | | | |

Figure 6

Results of the activity of compositions according to the present invention regarding the repellence against Anopheles gambiae:

| 1 | 2 | WS5 | | | | WS12 | | | | WS17 | | | | A | WS20 | | | |
|---|---|---|---|---|---|---|---|---|---|---|---|---|---|---|---|---|---|---|
| Product | | a | b | c | d | a | b | c | d | a | b | c | d | | a | b | c | d |
| 1 | 10 | 70 | 0 | 0 | 0 | 60 | 0 | 0 | 0 | 90 | 0 | 0 | 0 | 40 | 0 | 0 | 0 |
| 2 | 10 | 90 | 0 | 0 | 0 | 60 | 0 | 0 | 0 | 110 | 0 | 0 | 0 | 40 | 0 | 0 | 0 |
| 3 | 10 | 100 | 0 | 0 | 0 | 80 | 0 | 0 | 0 | 120 | 0 | 0 | 0 | 100 | 0 | 0 | 0 |
| 4 | 10 | 100 | 0 | 0 | 0 | 100 | 0 | 0 | 0 | 100 | 0 | 0 | 0 | 80 | 0 | 0 | 0 |
| 5 | 10 | 110 | 0 | 0 | 0 | 100 | 0 | 0 | 0 | 110 | 0 | 0 | 0 | 70 | 0 | 0 | 0 |
| 6 | 10 | 120 | 0 | 0 | 0 | 100 | 8 | 0 | 0 | 90 | 0 | 0 | 0 | 100 | 2 | 0 | 0 |
| 7 | 10 | 110 | 0 | 0 | 0 | 90 | 17 | 3 | 0 | 90 | 4 | 0 | 0 | 100 | 4 | 0 | 0 |
| 8 | 10 | 110 | 0 | 0 | 0 | 900 | 12 | 3 | 0 | 90 | 12 | 4 | 0 | 100 | 4 | 0 | 0 |
| 9 | 10 | 90 | 0 | 0 | 0 | 100 | 17 | 3 | 0 | 80 | 15 | 10 | 0 | 90 | 10 | 0 | 0 |
| 10 | 10 | 80 | 3 | 0 | 0 | 70 | 32 | 11 | 0 | 70 | 15 | 9 | 0 | 90 | 18 | 1 | 0 |
| 11 | 10 | 60 | 6 | 4 | 0 | 10 | 17 | 10 | 2 (1)* | 50 | 40 | | 1 (4)* | 80 | 22 | 6 | 0 |
| 12 | 10 | 60 | 24 | 18 | 4 (10)* | | | | | | | | | 60 | 45 | 21 | 4 (7)* |

Figure 7

COMPOSITION CONTAINING CITRONELLA JAVA OIL AND USE THEREOF FOR REPELLING INSECTS

This application is a National Stage Application of PCT/EP03/03944, filed Apr. 15, 2003, which claims priority from German Patent Application No. 102 19 109.3, filed Apr. 29, 2002.

BACKGROUND OF THE INVENTION

The present invention concerns an insect repellent (repellent) against flying, stinging, biting and sucking insects as well as pests of the genus acarina (mites and ticks).

Repellents are chemical substances which have a repulsive activity with respect to insects and arcarina. Practical importance has the use of these repellents in the field of human and veterinary hygiene in order to protect humans and animals from the activity of bloodsucking, stinging and biting pests, which are not only bothersome but also possess the potential to transmit diseases (malaria, FSME, lymeborreliose and others). Repellents which are to be used and applied directly on the skin must be compatible with the skin, non-toxic, lighffast and sweat fast and they also must be acceptable from a cosmetic standpoint, i.e. not problematic to the skin (drying, generation of wrinkles) as well as unproblematic from the pharmacological standpoint (irritation, penetration into deeper layers of the skin and penetration into the blood cycle or the lymph cycle). Furthermore, the protection of the treated areas of the skin or the protection of humans and animals by using treated products should be maintained as long as possible and the activity of the repellent should be as broad as possible, i.e. the repellent should be active against a lot of different pests.

In the past and as well as, to a lesser extent, at present, ethereal oils such as citronella oil and lemongrass oil as well as clove oil, lavender oil, eucalyptus oil, as well as camphor are used as repellents. These products, however, show the following drawbacks:

- they may contain problematic components, such as for example eugenol in clove oil, which has, in experiments shown mutagenic, carcinogenic and skin irritating activity, or cineol in the oil obtained from eucalyptus globulus, which immediately is able to give rise to tingling exanthemas,
- they may only show a short term activity, since the ethereal oils evaporate from the skin due to the body temperature, so that reapplication becomes necessary in order to obtain the desired protection,
- insufficient lightfastness may give rise to photosensitization as well as change of the product before application.

In the recent past, the above-discussed repellents have been replaced by synthetic repellents. Synthetic repellents known in the prior art are for example phthalic acid dimethyl esters, 1,2-ethylhexane-1,3-diol, 3,4-dihydro-2,2-dimethyl-4-oxo-2H-pyrane-6-carboxylic acid-n-butylester, succinic acid dipropylester, N,N-diethyl-3-methyl-benzamide (DEET, also named N,N-diethyl-m-toluamide) and pyridine-2,5-dicarboxylic acid-di-n-propylester (Ullmanns Encyclopedia of Technical Chemistry, $4^{th}$ edition, vol. 13, pages 237 and onwards, 1977). In the recent past, mainly hydroxyethyl-butyl-piperidine-carboxylate (1-piperidinecarboxylic acid-2-(2-hydroxyethyl)-1-methylpropylester) is used. However, these synthetic repellents often do not possess the required sweat fastness, irritate mucus membranes and are furthermore also able to penetrate through the uppermost layer of the skin, so that accumulation in the body may occur, in which connection must be noted that the resulting side effects have not yet been fully established although the general approach is that negative results are to expected.

SUMMARY OF THE PRESENT INVENTION

Accordingly, the object of the present invention is to provide an active insect repellent which can be applied directly to skin and/or to clothing and/or to other products which surround the user (bed linen, table cloth, tents and other materials) who seeks protection from bites and stings of insects and acarids (in particular ticks) which are either bothersome, harmful or may transmit diseases, on the basis of natural products or products identical to natural products having very low toxicological risks, which furthermore should provide a high activity over a prolonged time.

This object is solved in accordance with the present invention with an insect repellent as defined in claim 1. Preferred embodiments are defined in the sub-claims. The activity of the composition in accordance with the present invention is based on a specific composition of the substances, which themselves are since long known as insect repellents, which, however, due to their short term duration and therefore insufficient activity have never been used or are not used at present.

BRIEF DESCRIPTION OF THE DRAWINGS

FIGS. 1, 2a, 2b, 3a, 3b, 3c, and 4–7 are tables of test results showing the effectiveness of the compositions of the present invention with respect to mosquitoes.

DETAILED DESCRIPTION OF THE PRESENT INVENTION

In the following the single components to be used in accordance with the composition of the present invention are described.

The citronella oil (the German designation Bartgrasöl is also used) is a natural product which can be obtained usually by steam distillation of a suitable raw material. This natural product contains as main components citronellal, geraniol, borneol and citronellol, together with further terpene derivatives. The desired activity in accordance with the present invention, however, in accordance with the definition in the claim, is only shown by citronella oil which is the citronella java oil from *cymbopogon winterianus jowitt*. This plant, from which the ethereal oil which is active in accordance with the present invention is obtained, can be found on the isle of Bali as well as several isles in the vicinity thereof. This product may, for example, be obtained commercially from the company Düllberg-Konzentra (Hamburg). Surprisingly, the citronella indonesia oil obtained from *cymbopogon nardus* does not show the desired activity.

The vegetable triglyceride used in accordance with the present invention may be any vegetable triglyceride. Preferably, the vegetable triglyceride is, however, coconut and/or soybean oil, which may be employed singly or in mixture. The two preferred oils are, with respect to their activity within the composition in accordance with the present invention, comparable. In addition to natural coconut oil and natural soybean oil, respectively, the present invention also comprises the use of mixtures which are identical to the natural products obtained from synthetic or natural triglycerides, which correspond in their mixture to the natural products.

Coconut oil is a lardy, soft, white to weak yellow oil, having a melting point of from 20 to 23° C. Coconut oil may be obtained by pressing and extraction of the seeds of the coconut tree. Coconut oil is a mixture of different triglycerides, the exact composition varies in dependency from the place of origin and the conditions during growth. A typical composition is shown in the following:

Table 1

| Fatty acid | content (wt. %) |
| --- | --- |
| Hexanoic acid | 0.2–1.0 |
| Octanoic acid | 5.4–8.0 |
| Decanoic acid | 6.5–8.5 |
| Lauric acid | 45.0–51.0 |
| Myristic acid | 16.5–18.5 |
| Palmitic acid | 9.0–10.5 |
| Stearic acid | 2.0–2.3 |
| Behenic acid | 0.2–0.4 |
| Oleic acid | 8.0–10.0 |
| Linolic acid | 0.7–1.0 |

The soy bean oil used in accordance with the present invention is a natural product which occurs mainly in the form of a yellowish or brown-yellow fatty and half dry oil, which can be obtained by pressing and/or extraction with hydrocarbons, using soy beans or braised soy beans. Also soybean oil is a mixture of different triglycerides, which composition again differs in dependency from the starting products. A typical composition, which shows, however, only the main components, is shown in the following.

Table 2

| Fatty acid (number of carbon atoms:number of double bonds) | content (wt. % (most common value)) |
| --- | --- |
| C16:0 | 7.0–14 (10) |
| C18:0 | 1.4–4.5 (4.0) |
| C18:1 | 19–30 (21) |
| C18:2 | 44–62 (56) |
| C18:3 | 4–11 (8) |

In addition to the above-mentioned fatty acids, soy bean oil comprises lesser amounts of fatty acids having 14 or fewer carbon atoms (less than 0.6 wt %), a small amount of C16 fatty acids having one double bond (less than 0.5 wt %) as well as a low amount of fatty acids having 20 or 22 carbon atoms and 0 or 1 double bond, respectively (each less than 1.0 wt %).

The organic acid to be used in accordance with the present invention may be any naturally occurring or synthetically prepared acid. Preferred are, in accordance with the present invention, organic acids, selected from the group of citric acid, benzoic acid, lactic acid, sorbic acid, malic acid, tartaric acid, maltonic acid, fumaric acid and succinic acid, wherein in particular due to toxicological and dermatological reasons, citric acid, benzoic acid, lactic acid, sorbic acid, malic acid and tartaric acid are preferred, from which citric acid, malic acid and lactic acid are in particular preferred.

In addition to the above-mentioned essential components, the composition in accordance with the present invention may contain further additives, which depend from the desired type of the composition. Preferred additional components are monosodium carbonate (preferred in an amount of from 0.5 to 2.0 wt % in particular 0.8 to 1.2 wt %) as well as castor oil products (in particular hydrogenated castor oil with polyethylene glycol (40)) (preferably in an amount from 1.5 to 4.0 wt %, more preferably 2.0 to 2.5 wt %). The monosodium carbonate serves as agent to adjust the pH value to the range of from 5.5 to 6, which is usual in the field of cosmetic preparations. The castor oil derivatives on the other hands are effective emulsifying agents, which have been approved for use in the field of foods and cosmetics and pharmaceutical preparations. Due to the effective dispersion in the form of droplets, which may be obtained when using this emulsifying agent, the stability of the emulsion of the composition in accordance with the present invention, if present in the form of an emulsion, is improved, which secures at the same time the uniform distribution of the active components, so that, for example when the composition is packed in a bottle, it is secured that every part taken out of the bottle has the composition as the total content of the bottle.

Furthermore, the present invention provides the use of the composition in accordance with the present invention as insect repellent. All embodiments defined as preferred in connection with the composition in accordance with the present invention are also designated herewith as preferred for the use in accordance with the present invention.

The later shown test series show (see section Examples) that the substances in pure form or in the form of mixtures outside of the specific composition in accordance with the present invention, even when adding the further additives which may be employed in accordance with the present invention, do not show a sufficient activity.

In this respect, it therefore must be regarded as surprising that the composition in accordance with the present invention, as shown by the test series (even when adding additional additives which themselves do not show any insect repellent activity) show activities which are not only superior to the natural products named above but also superior to the synthetic repellents.

The single components of the composition in accordance with the present invention are contained in the composition in the amounts as defined in claim 1. Preferred amounts for the ethereal citronella java oil are 7.5 to 30 wt %, preferably 10 to 20 wt %. The vegetable triglyceride preferably is present in an amount of from 4.5 to 15 wt %, more preferably in an amount of from 4.5 to 10.5 wt %. The organic acid to be used in accordance with the present invention preferably is present in an amount of from 0.5 to 4.4 wt %, more preferably 1 to 2 wt %.

The solvent used in accordance with the present invention and the carrier substance to be used in accordance with the present invention, respectively, preferably is water or an aqueous solution of an organic solvent. Water is preferred as solvent.

The carrier substance to be used in accordance with the present invention may be a known solid carrier, which does not exert any impairing activity on the composition in accordance with the present invention. Suitable carrier substances can be selected among inorganic oxides and other solid carrier substance known in the field of pharmaceutical preparations.

Preferred Compositions in Accordance with the Present Invention Comprise:
- 4.5 to 50 wt % citronella oil
- 3 to 30 wt % coconut oil and/or soy bean oil
- 10 to 92.4 wt % water and
- 0.1 to 10 wt % citric acid Preferably a Composition in Accordance with the Present Invention Comprises:
- 7.5 to 30 wt % citronella oil
- 4.5 to 15 wt % coconut oil/soy bean oil
- 50 to 87 wt % water and
- 0.5 to 4.5 wt % citric acid More Preferably a Composition in Accordance with the Present Invention Comprises:
- 10 to 20 wt % citronella java oil
- 4.5 to 10.5 wt % coconut oil/soy bean oil
- 68 to 84 wt % water and
- 1 to 2 wt % citric acid Furthermore, the present invention provides a method for preparing the composition in accordance with the present invention. In order to obtain a suitable stable product, the process for preparation is suitably carried out in accordance with the following process:

a) within a vessel which may be closed tightly the vegetable triglyceride, preferably coconut oil and/or soy bean oil is stirred and melted at 80° C.

b) the organic acid is dissolved in cold water and is introduced with stirring into the melt of the fat, subsequently c) the citronella oil is introduced with stirring and stirring is continued for 5 hours at 80° C. in order to obtain a stable emulsion, followed d) by cooling to 25° C. with stirring.

The process for preparing the composition is possible in any of the known devices used in the field of cosmetics or pharmaceutical preparations.

The preparation can be varied in accordance with the knowledge of the skilled person using conventional process steps in order to obtain the composition in accordance with the present invention in the form of an emulsion, a dispersion, a lotion, a cream, a gel or a solution. The advantages of each of the forms are evident with respect to the desired type of application.

For preparing these forms, all usual processes for preparation may be used. Furthermore, all known and usual basic materials and additives may be employed.

These materials comprise the usual and common additives used for chemical and technical preparations as well as cosmetic and pharmaceutical preparations, selected among solvents, solubility promoter, solution aids, emulsifying agents, wetting agents, anti-foaming agents, salt-forming agents, buffers, gel-forming agents, film-forming agents, thickeners, binders, lubricants, spreadability improving agents, anti-stick agents, flow regulating agents, desiccants and humidifying agents, acidic and basic pH adjusting agents, such as organic acids and fruit acids or hydroxides of earth alkaline metals, amines and amides, fillers and auxiliary agents, such as antioxidants, preservatives, odor correcting agents and colorants.

The term "emulsion" in the present case comprises all dispersed systems of two or more liquids which are not miscible, wherein the emulsion components may be present at room temperature also as solids or as amorphous or crystalline waxes. The emulsions may be macro emulsions or micro emulsions. Typically, water in oil and/or oil-in-water emulsions are used. In order to reduce the interfacial energy (energy required for emulsifying) emulsifying agents are used.

Emulsifying agents are typically surface-active compounds, typically comprising hydrophilic terminal groups. Typical examples comprise:

anionic emulsifying agents, i.e. emulsifying agents having carboxylate, sulfonate, sulfate, phosphate, polyphosphate, lactate, citrate, tartrate, glucose or polyglucose terminal groups cationic emulsifying agents, i.e. emulsifying agents having amine salt or quaternary ammonium terminal groups amphoteric or zwitterionic emulsifying agents, i.e. emulsifying agents having zwitterionic or betainic terminal groups, as well as non-ionic emulsifying agents, i.e. emulsifying agents having alcohol, polyether, glycerine, sorbit, pentaerythrit, saccharose, acetic acid and/or lactic acid residues in the terminal groups.

All emulsifying agents furthermore comprise lipophilic terminal groups, such as alkyl residues or alkylene residues, which may be straight chain, branched or cyclic, as well as aryl residues and alkaryl residues.

Furthermore, hydrophilic side chain groups, such as hydroxyl groups, ester groups, sulfamide groups, amide groups, amine groups, polyamide-polyamine-groups, ether groups, polyether, glycerin groups, sorbit groups, pentaerythrit groups or saccharose groups can be contained.

The term "gel" defines in relation to the present invention dimensionally stable systems which are easily deformable and which are liquid rich, comprising at least two components. Typically, these two components are the following: a) a liquid and b) a solid, colloidal dispersed compound, such as gelatine, silicic acid, montmosillonit, bentonit, polysaccharide, polyacrylate, pectin and the like. The liquid a) may be, in the present case, the composition in accordance with the present invention.

The following examples illustrate the present invention. In this connection, the following compositions were prepared.

1.) All examples presented under the designation PC (1 to 16) relate to single substances or mixtures thereof outside the scope of the compositions according to the present invention, although theses mixtures have been prepared according to the process disclosed as process in accordance with the present invention.

These comparative examples do show beyond any doubt that only compositions in accordance with the present invention do show the desired activity:

PC 1=100,00 wt. % Citronella Java Oil from *Cymbopogon winterianus Jowitt*

PC 2=100,00 wt. % coconut oil, purified and hydrogenated, Feed Grade

PC 3=100,00 wt. % soybean oil, Feed Grade

PC 4=100,00 wt. % citric acid, 60% solution in water

PC 5=51,00 wt. % Citronella Java Oil +49,00 wt. % coconut oil

PC 6=51,00 wt. % Citronella Java Oil +49,00 wt. % soybean oil

PC 7=51,00 wt. % Citronella Java Oil +31,00 wt. % coconut oil +18,00 wt. % water PC 8=51,00 wt. % Citronella Java Oil +31,00 wt. % soybean oil +18,00 wt. % water PC 9=4,00 wt. % Citronella Java Oil +31,00 wt. % coconut oil +64,50 wt. % of a 60% solution of citric acid in water (36,00% citric acid +24,00% water)

PC10=4,00 wt. % Citronella Java Oil +31,00 wt. % coconut oil +64,50 wt. % of a 0,10% solution of citric acid in water (0,065% citric acid +64,935% water)

PC11=51,00 wt. % Citronella Java Oil +2,00 wt. % soybean oil +47,00 wt. % of a 40% solution of citric acid in water (18,80% citric acid +28,20% water)

PC12=51,00 wt. % Citronella Java Oil +2,00 wt. % soybean oil +47,00 wt. % of a 0,15% solution of citric acid in water (0,094% citric acid +46,906% water)

PC13=51,00 wt. % Citronella Java Oil +2,50 wt. % coconut oil +2,50 wt. % monosodium carbonate +10,50 wt. % citric acid +33,50 wt. % water PC14=4,00 wt. % Citronella Java Oil +15,50 wt. % coconut oil +15,50 wt. % soybean oil +2,50 wt. % monosodium carbonate +0,09 wt. % citric acid +62,41 wt. % water PC15=51,00 wt. % Citronella Java Oil +1,25 wt. % coconut oil +1,25 wt. % soybean oil +2,50 wt. % monosodium carbonate +10,50 wt. % citric acid +4,50 wt. % PEG-40 hydrogenated Castor Oil (USP) +28,50 wt. % water PC16=4,00 wt. % Citronella Java Oil +15,50 wt. % coconut oil +15,50 wt. % soybean oil +2,50 wt. % monosodium carbonate +0,09 wt. % citric acid +4,50 wt. % PEG-40 hydrogenated Castor Oil (USP) +57,41 wt. % water 2.) The product tested under the designation REF is ANTI BRUMM which is a commercial product, which is known as one of the most effective/active on the market. It contains as active agent 30,00 wt. % DEET (Diethyl-toluamide) and shows in comparison to the compositions according to the present invention an equal or clearly inferior activity.

3.) All examples presented with the designation WS are compositions in accordance with the present invention:

WS 1=4,50 wt. % Citronella Java Oil +3,50 wt. % coconut oil +0,10 wt. % citric acid +91,90 wt. % water WS 2=4,50 wt. % Citronella Java Oil +3,50 wt. % soybean oil +0,10 wt. % citric acid +91,90 wt. % water WS 3=4,50 wt. % Citronella Java Oil +30,00 wt. % coconut oil +0,10 wt. % citric acid +65,40 wt. % water WS 4=4,50 wt. % Citronella Java Oil +30,00 wt. % soybean oil +0,10 wt. % citric acid +65,40 wt. % water WS 5=50,00 wt. % Citronella Java Oil +3,00 wt. % coconut oil +10,00 wt. % citric acid +37,00 wt. % water WS 6=50,00 wt. % Citronella Java Oil +3,00 wt. % soybean oil +10,00 wt. % citric acid +37,00 wt. % water WS 7=50,00 wt. % Citronella Java Oil +30,00 wt. % coconut oil +10,00 wt. % citric acid +10,00 wt. % water WS 8=50,00 wt. % Citronella Java Oil +30,00 wt. % soybean oil +10,00 wt. % citric acid +10,00 wt. % water WS 9=7,50 wt. % Citronella Java Oil +4,50 wt. % coconut oil +0,50 wt. % citric acid +87,00 wt. % water WS 10=7,50 wt. % Citronella Java Oil +14,50 wt. % coconut oil +4,50 wt. % citric acid +72,50 wt. % water WS 11=30,00 wt. % Citronella Java Oil +4,50 wt. % soybean oil +4,50 wt. % citric acid +60,00 wt. % water WS 12=30,00 wt. % Citronella Java Oil +14,50 wt. % soybean oil +4,50 wt. % citric acid +50,00 wt. % water WS 13=10,00 wt. % Citronella Java Oil +4,50 wt. % coconut oil +1,00 wt. % citric acid +84,00 wt. % water WS 14=10,00 wt. % Citronella Java Oil +10,00 wt. % coconut oil +2,00 wt. % citric acid +68,00 wt. % water WS 15=20,00 wt. % Citronella Java Oil +4,50 wt. % soybean oil +1,00 wt. % citric acid +84,00 wt. % water WS 16=20,00 wt. % Citronella Java Oil +10,00 wt. % soybean oil +2,00 wt. % citric acid +68,00 wt. % water WS 17=12,50 wt. % Citronella Java Oil +10,00 wt. % coconut oil +1,25 wt. % citric acid +0,90 wt. % monosodium carbonate +75,35 wt. % water WS 18=12,50 wt. % Citronella Java Oil +10,00 wt. % soybean oil +1,25 wt. % citric acid +0,90 wt. % monosodium carbonate +2,50 wt. % PEG-40 hydrogenated Castor Oil (USP) +72,85 wt. % water WS 19=10,00 wt. % Citronella Java Oil +7,50 wt. % coconut oil +1,00 wt. % citric acid +0,70 wt. % monosodium carbonate +2,00 wt. % PEG-40 hydrogenated Castor Oil (USP) +78,80 wt. % water WS 20=15,00 wt. % Citronella Java Oil +10,00 wt. % soybean oil +1,50 wt. % citric acid +1,00 wt. % monosodium carbonate +3,00 wt. % PEG-40 hydrogenated Castor Oil (USP) +69,50 wt. % water Test Series for the Evaluation of the Repellent Activity with Respect to Mosquitoes 1.Experimental Arrangement:

All tests were carried out in accordance with the experimental direction of the Swiss Tropic Institute, using a standardized method in order to achieve comparable and reproducible results. As testing animals exclusively female adult, i.e. sexually mature and therefore blood seeking specimen of *Aedes aegypti* (yellow fever mosquitoes) which were raised in the laboratory and, for the products evaluated as active, adequate specimens of the type *Anopheles gambiae* (fever mosquitoes) were used, since these two types, due to the transfer of malaria and yellow fever, present the highest potential heath risk for humans.

In a breeding cage with a dimension of 40×40×40 cm, 400 mosquitoes were placed, which have not received, for one day, the usually employed sugar containing water, which increases their aggressive behavior. This corresponds to a very high population density, which usually does not occur in nature so that a secure differentiation with respect to the activity of the tested composition can be carried out.

As test persons, students majoring in biology and zoology were used, which participated on their will and which were, due to their experience, able to carry out the test series with the required scientific accuracy.

For each test day, each of the two forearms of the respective test person was treated on an area of 250 cm² with the selected test product and the remaining part of the arm was covered and marked accordingly. An amount of 2 ml of the respective test composition was applied evenly onto the test area. The treated area of the forearm was closed in direction to the hand and in direction to the remaining arm using an adhesive and short plastic hoses, which did not enable mosquitoes to sting through onto the untreated area. The non-treated hand was covered with a thick glove and, in this respect, serves as a control of the biting activity of the mosquitoes, since the mosquitoes try to sit on the glove and attempted to bite through the glove into the skin below.

For each test, the hand and the treated forearm, after a one hour waiting period after the application of the composition, first the left forearm then the right forearm, were held for ten minutes each into the cage and during this time, the numbers of mosquitoes were noted which (a) tried to bite through the glove (positive control)
(b) flew towards the treated area but turned away in a distance of below 3 cm (repulsive activity)
(c) sat down on the treated area for more than 2 seconds but did not bite and
(d) sat down on the treated area, attempted to bite and suck blood.

This procedure was carried out until one or more mosquitoes satisfied criterion (d).

Each test person did only carry out one test per day in order to reduce the danger of product accumulation and the risk of cross reactions of products due to insufficient cleaning of skin.

Products having a very bad activity and products with a very good activity were tested on another day again in order to prevent wrong results due to application errors, loss of product etc. These confirmatory tests were carried using a different test person. These confirmatory tests were carried out for products PC1, PC2, PC3 and PC4, which showed surprisingly bad results and with respect to products WS17, WS18, WS19 and WS20, which showed a surprising and unexpected high activity potential.

The evaluation of all experimental results clearly reveals that the compositions in accordance with the present invention WS show a non-obvious activity with respect to the repellence regarding bloodsucking mosquitoes presenting health risks, not only with respect to similar compositions PC which are, however, not within the scope of the compositions as defined in the claims, but as well with respect to the established commercial product REF.

2. Test Results: The Results are Summarized in FIGS. 1–7.

Legends:
1: Time after application of the respective test products in hours
2: Duration of exposition within the ten-minute test duration each hour; if bites were detected, the process was stopped and the shortened duration of exposition as shown
a: Mosquitoes sitting down on the glove
b: Mosquitoes flying to the treated area but which turned away within a distance of 3 cm without sitting down or mosquitoes sitting down for less than 2 seconds
c: Mosquitoes sitting down on the treated area for longer than 2 seconds which, however, did not bite and therefore are summarized with mosquitoes satisfying criterion b as nuisance factor
d: Number of biting mosquitoes prior to the stoppage of the experiment
: Result could not be obtained in view of the short period until the first bite occurred
*: Stoppage due to bites Also the confirmatory tests (FIG. 4) confirmed the surprisingly high activity of the compositions according to the present invention WS17 to WS20, although they had only comparably low contents of active agents.

Test series concerning the activity of compositions in accordance with the present invention in comparison to an untreated control and a reference product regarding the repellence concerning ticks using a laboratory test and guinea pigs In total, 12 adults female guinea pigs obtained a treatment in order to remove the hair on an area of 4×4 cm on the right limb. Onto the skin and the surrounding areas still containing hair, 2 ml of the respective test product were applied by hand. Subsequently, one adult tick which had not received any food for two weeks and which has been raised in a laboratory was placed every hour in the middle of the hairless area using tweezers. The tick was a tick of the type *Ixodes ricinus*. The behavior of the ticks was observed. The guinea pigs were, contrary to other laboratory studies, not sedated in order to emulate a natural situation. During the test, the guinea pigs were fed with salad and they remained relatively calm since they were used to humans.

Immediately after the application of the ticks, it is was evident that the ticks did not start, as usual, to wander around in order to look for a suitable place for biting (usually a place under the leg), as it was observed with the non-treated guinea pig which served as control (KT). Instead, the ticks over a period of several minutes, did conduct a circular movement in the middle of the treated area. After those minutes, even a subtle movement of the guinea pigs led to the fact that the ticks fell off the guinea pigs, although ticks have the possibility to maintain their position even on smooth surfaces with their claws. The ticks which have fallen off the guinea pigs were placed into glasses and were observed for 72 hours. All ticks were dead after this observation.

Tested Products and Designation of Tests Animals:
the non-treated control is designated KT
the animals treated with the reference product ANTI BRUMM is designated REF and
the animals treated with compositions in accordance with the present invention are designated WS3, WS7, WS9, WS12, WS14, WS16, WS17, WS19 and WS20.

Results of the Activity Tests:

KT: each of the ticks applied over the test duration of 8 hours, after a short orientation phase, started to bite and to suck blood, whereupon they were immediately removed from the animal in order to prevent any weakening of the animal.

REF: the ticks of the first two hours fell off, as observed with the products of the series WS, and also these ticks were dead within the observation period of 72 hours. The ticks of the third hour start to bite, leading to the stop of the experiment. The protection duration therefore is two hours.

Protection Duration of Composition According to the Present Invention Against Ticks on Guinea Pigs X=protection duration
Y=time of the first drilling of a freshly placed tick

|  | Product | | | | | | | | | |
|---|---|---|---|---|---|---|---|---|---|---|
|  | WS3 | WS7 | WS9 | WS12 | WS14 | WS16 | WS17 | WS18 | WS19 | WS20 |
| 1 h |  |  |  |  |  |  |  |  |  |  |
| 2 h |  |  |  |  |  |  |  |  |  |  |
| 3 h | x |  |  |  |  |  |  |  |  |  |
| 4 h | y |  | X |  | x |  |  |  |  |  |
| 5 h |  |  | Y |  | y | X | x |  | x |  |
| 6 h |  |  |  | x |  | Y | y | x | y |  |
| 7 h |  | x |  | y |  |  |  | y |  | x |
| 8 h |  | y |  |  |  |  |  |  |  | y |

All ticks which fell off without attempting to drill were found to be dead after the observation period of 72 hours.

The invention claimed is:

1. Composition, comprising 4.5–50 weight (wt.) % ethereal Citronella Java Oil of *Cymbopogon Winterianus Jowitt*, 3–30 wt. % vegetable triglyceride and 0.1–10 wt. % of at least one organic acid, and a solvent and/or a carrier substance.

2. The composition according to claim 1, wherein the vegetable triglyceride is coconut oil.

3. The composition according to claim 1, wherein the vegetable triglyceride is soybean oil.

4. The composition according to claim 1, wherein the composition is present in the form of an aqueous solution.

5. The composition according to claim 1, wherein the composition is present in the form of an emulsion, a dispersion, a lotion, a cream, a solution, or a gel.

6. A method to repel insects comprising applying an effective amount of the composition of claim 1 to a person, product and/or an area.

7. The composition according to claim 2, wherein the composition is present in the form of an aqueous solution.

8. The composition according to claim 3, wherein the composition is present in the form of an aqueous solution.

9. The composition according to claim 2, wherein the composition is present in the form of an emulsion, a dispersion, a lotion, a cream, a solution, or a gel.

10. The composition according to claim 3, wherein the composition is present in the form of an emulsion, a dispersion, a lotion, a cream, a solution, or a gel.

11. The composition according to claim 4, wherein the composition is present in the form of an emulsion, a dispersion, a lotion, a cream, a solution, or a gel.

12. A method to repel insects comprising applying an effective amount of the composition of claim 2 to a person, product, and/or an area.

13. A method to repel insects comprising applying an effective amount of the composition of claim 3 to a person, product, and/or an area.

14. A method to repel insects comprising applying an effective amount of the composition of claim 4 to a person, product, and/or an area.

15. A method to repel insects comprising applying an effective amount of the composition of claim 5 to a person, product, and/or an area.

16. The method of claim 6, wherein said composition is applied to the skin or clothing of a person.

17. The composition of claim 1, wherein said organic acid is citric acid.

18. The composition of claim 1, wherein the organic acid is citric acid, benzoic acid, lactic acid, sorbic acid, malic acid, tartaric acid, maltonic acid, fumaric acid, succinic acid, or any combination thereof.

19. The composition of claim 1, wherein the composition comprises 4.5 to 50 wt % citronella oil, 3 to 30 wt % coconut and/or soy bean oil, 10 to 92.4 wt % water, and 0.1 to 10 wt % citric acid.

20. The composition of claim 1, wherein the composition comprises 7.5 to 30 wt % citronella oil, 4.5 to 15 wt % coconut and/or soy bean oil, 50 to 87 wt % water, and 0.5 to 4.5 wt % citric acid.

21. The composition of claim 1, wherein the composition comprises 10 to 20 wt % citronella oil, 4.5 to 10.5 wt % coconut and/or soy bean oil, 68 to 84 wt % water, and 1 to 2 wt % citric acid.

\* \* \* \* \*